United States Patent
Heiskanen et al.

(10) Patent No.: US 10,900,169 B2
(45) Date of Patent: Jan. 26, 2021

(54) METHOD AND INTERMEDIATE FOR THE PRODUCTION OF HIGHLY REFINED OR MICROFIBRILLATED CELLULOSE

(71) Applicant: STORA ENSO OYJ, Helsinki (FI)

(72) Inventors: Isto Heiskanen, Imatra (FI); Cecilia Land Hensdal, Forshaga (SE); Lars Axrup, Hammarö (SE); Heidi Saxell, Vantaa (FI)

(73) Assignee: STORA ENSO OYJ, Helsinki (FI)

( * ) Notice: Subject to any disclaimer, the term of this patent is extended or adjusted under 35 U.S.C. 154(b) by 331 days.

(21) Appl. No.: 14/421,708

(22) PCT Filed: Aug. 16, 2013

(86) PCT No.: PCT/FI2013/050805
§ 371 (c)(1),
(2) Date: Feb. 13, 2015

(87) PCT Pub. No.: WO2014/029909
PCT Pub. Date: Feb. 27, 2014

(65) Prior Publication Data
US 2015/0218757 A1   Aug. 6, 2015

(30) Foreign Application Priority Data
Aug. 20, 2012   (FI) ..................................... 20125864

(51) Int. Cl.
| | | |
|---|---|---|
| *D21C 9/00* | (2006.01) | |
| *D21H 11/18* | (2006.01) | |
| *D21C 5/00* | (2006.01) | |
| *D21C 9/18* | (2006.01) | |
| *C08L 1/02* | (2006.01) | |
| *C12P 19/04* | (2006.01) | |
| *C12P 19/14* | (2006.01) | |
| *D21H 17/00* | (2006.01) | |
| *D21H 17/67* | (2006.01) | |

(52) U.S. Cl.
CPC ............... *D21C 9/007* (2013.01); *C08L 1/02* (2013.01); *C12P 19/04* (2013.01); *C12P 19/14* (2013.01); *D21C 5/005* (2013.01); *D21C 9/002* (2013.01); *D21C 9/005* (2013.01); *D21H 11/18* (2013.01); *D21H 17/005* (2013.01); *D21H 17/675* (2013.01); *D21H 17/74* (2013.01); *C08L 2205/16* (2013.01); *D21C 9/18* (2013.01)

(58) Field of Classification Search
CPC ........ D21C 9/007; D21C 9/002; D21C 9/004; D21C 9/005
See application file for complete search history.

(56) References Cited

U.S. PATENT DOCUMENTS

| | | |
|---|---|---|
| 2,958,433 A | 11/1960 | Borthen et al. |
| 3,047,453 A | 7/1962 | Shook, Jr. |
| 3,382,140 A | 5/1968 | Henderson et al. |
| 4,260,452 A * | 4/1981 | Kruger ..................... D21C 5/00 162/23 |
| 4,374,702 A | 2/1983 | Turbak et al. |
| 4,481,076 A | 11/1984 | Herrick |
| 4,481,077 A | 11/1984 | Herrick |
| 5,964,983 A | 10/1999 | Dinand et al. |
| 6,146,494 A * | 11/2000 | Seger ..................... D21C 5/005 162/100 |
| 6,231,657 B1 | 5/2001 | Cantiani et al. |
| 6,602,994 B1 | 8/2003 | Cash et al. |
| 7,364,639 B2 | 4/2008 | Hu et al. |
| 8,546,558 B2 * | 10/2013 | Ankerfors ............... D21H 11/18 536/56 |
| 2003/0000665 A1 | 1/2003 | Takai et al. |
| 2003/0131958 A1 * | 7/2003 | Jaschinski .............. D21C 9/004 162/65 |
| 2005/0074542 A1 | 4/2005 | Lundberg et al. |
| 2005/0194477 A1 * | 9/2005 | Suzuki ..................... D21D 1/30 241/20 |

(Continued)

FOREIGN PATENT DOCUMENTS

| | | | |
|---|---|---|---|
| CA | 758488 A * | 5/1967 | |
| DE | 2628221 A1 | 1/1978 | |

(Continued)

OTHER PUBLICATIONS

SMOOK, Handbook for Pulp and Paper Technologists, 1992, Angus Wilde Publications, 2nd edition, chapter 9.*
SMOOK, Handbook for Pulp and Paper Technologists, 1992, Angus Wilde Publications, 2nd edition, chapter 11. (Year: 1992).*
Beltramino et al., Facilitating the selection of raw materials: Evaluation of the effects of TCF and ECF bleaching sequences on different wood and non-wood pulps, Jun. 2018,AFINIDAD LXXV (Year: 2018).*
Supplementary European Search Report for European patent application No. 13830431.6, dated Mar. 15, 2016, 7 pages.

(Continued)

*Primary Examiner* — Anthony Calandra
(74) *Attorney, Agent, or Firm* — Patterson Thuente Pedersen, P.A.

(57) ABSTRACT

A method for the production of highly refined or microfibrillated cellulose (MFC), comprising the steps of treating cellulosic fibres to remove at least a major part of the primary wall of the fibres, drying the treated fibres, rewetting the treated fibres, and disintegrating the wetted fibres by mechanical means to obtain the final product. Dried cellulosic pulp is produced as an intermediate product of the method, having an average fibre length of at least 0.4 mm, while less than 50% of the primary wall material of natural untreated fibres is left in the intermediate product. Instead of transporting large amounts of dilute MFC dispersion the invention enables transport of the dry intermediate product to the MFC end user, who would complete the process by turning the intermediate product to final MFC by use of standard disintegrating devices.

18 Claims, No Drawings

(56) References Cited

U.S. PATENT DOCUMENTS

| | | | |
|---|---|---|---|
| 2007/0111920 | A1 | 5/2007 | Bauer et al. |
| 2008/0073043 | A1 | 3/2008 | Greschik et al. |
| 2012/0135506 | A1 | 5/2012 | Heiskanen et al. |
| 2012/0136146 | A1 | 5/2012 | Heiskanen et al. |
| 2012/0160433 | A1 | 6/2012 | Vehvilainen et al. |
| 2015/0152598 | A1 * | 6/2015 | Mitchell ............. C08H 6/00 162/56 |
| 2015/0167243 | A1 * | 6/2015 | Bilodeau ............. D21C 5/005 162/65 |

FOREIGN PATENT DOCUMENTS

| | | | |
|---|---|---|---|
| EP | 1316639 | | 6/2003 |
| EP | 1936032 | A1 | 6/2008 |
| JP | S59-189141 | A | 10/1984 |
| JP | 2008-1728 | A | 1/2008 |
| JP | 2010-235669 | A | 10/2010 |
| WO | WO 98/56981 | | 12/1998 |
| WO | WO 2007/001229 | A1 | 5/2006 |
| WO | WO 2010/092239 | A1 | 8/2010 |
| WO | WO2010102802 | | 9/2010 |
| WO | WO 2010/116826 | A1 | 10/2010 |
| WO | WO 2010/12547 | A2 | 11/2010 |
| WO | WO 2011 004301 | A1 | 1/2011 |
| WO | WO 2011004301 | A1 * | 1/2011 ............. D21C 5/005 |
| WO | WO2011140643 | | 11/2011 |
| WO | WO2011141877 | | 11/2011 |
| WO | WO 2012/107642 | A1 | 8/2012 |
| WO | WO 2012/107643 | A2 | 8/2012 |
| WO | WO2013090272 | | 6/2013 |

OTHER PUBLICATIONS

International Search Report for PCT/FI2013/050805, dated Dec. 11, 2013, 4 pgs.

Written Opinion of the International Searching Authority for PCT/FI2013/050805, dated Dec. 11, 2013, 7 pgs.

Search Report issued in Finnish Application No. 20125864, dated Jun. 19, 2013, 2 pgs.

Office Action issued in Finnish Application No. 20125864, dated Jun. 19, 2013, 7 pgs.

Sjoberg, J "5.5 A new method for the determination of carbohydrates in surface layers of fibers (paper VI)" in: Characterization of chemical pulp fiber surfaces with an emphasis on the hemicelluloses: Royal Institute of Technology (KTH), Department of Fibre and Polymer Technology, Doctoral Thesis, 2002, Trita-PMT. 2002:12, pp. 40-41.

Sjoberg, J et al. "Analyses of carbohydrates and lignin in the surface and inner layers of softwood pulp fibres obtained employing various alkaline processes", Nordic pulp and paper research journal (NPPRJ), 2002, vol. 17, No. 3, pp. 295-301, ISSN (online) 2000-0669, p. 296.

JP Office Action (2015-527949) dated Sep. 12, 2017; pp. 1-4.

English Translation of JP Office Action (2015-527949); dated Sep. 12, 2017; pp. 1-5.

Sjöberg et al., "Analyses of carbohydrates and lignin in the surface and inner layers of softwood pulp fibers obtained employing various alkaline cooking processes," Nordic Pulp and Paper Research Journal, vol. 17, No. 3, 2002, pp. 295-301.

Japanese Office Action and English translation for Japanese patent application No. 2015-527949, dated Apr. 11, 2017, 14 pages.

Astraiankis et al., "Sheet Production and Converting.: Market Pulp, Paper, Paperboard", Mar. 28, 2011.

Chen et al., Cellulose (Dissolving Pulp) Manufacturing Processes and Properties: A Mini-Review. bioresources.com(2016).

Henriksson et al., "An environmentally friendly method for enzyme-assisted preparation of micofibrillated cellulose (MFC) nanofibers", ScienceDirect. (2007).

Deshpande, The initial phase of sodium sulfite pulping of softwood: a comparison of different pulping options. Diss. Karlstads universitet. Nov. 25, 2016.

Svensson, "Nanocomposites made from nanoporous cellulose fibre", Diss. KTH Royal Institute of Technology. Oct. 26, 2012.

Gullichsen et al (editor), Larsson/Karisson "Papermaking Science and Technology", Book 6A, Chemical Pulping, Chapter 10: Pulp Drying Applications. pp. A667-A686. © 1999.

U.S. Appl. No. 13/323,136, filed Dec. 12, 2011, inventors Tausche et al.

European Patent Office Notice of Opposition (BillerudKorsnäs AB) for European Application No. 13830431.6 dated Feb. 4, 2009.

European Patent Office Notice of Opposition (FiberLean Technologies Limited) for European Application No. 13830431.6 dated Feb. 4, 2009.

Spence et al., "The effect of chemical composition on microfibrillar cellulose films from wood pulps: water interactions and physical properties for packaging applications" (2010).

European Patent Office Letter accompanying subsequently filed items for European Application No. 13830431.6 dated Feb. 20, 2019.

* cited by examiner

METHOD AND INTERMEDIATE FOR THE PRODUCTION OF HIGHLY REFINED OR MICROFIBRILLATED CELLULOSE

RELATED APPLICATIONS

This application is a National Phase entry of PCT Application No. PCT/FI2013/050805, filed Aug. 16, 2013, which claims priority from Finland Application No. 20125864, filed Aug. 20, 2012, the disclosures of which are hereby incorporated by referenced herein in their entirety.

FIELD OF THE INVENTION

The present invention relates to a method for the production of highly refined or microfibrillated cellulose. Furthermore, the present invention covers a dried cellulosic pulp, which is obtainable as an intermediate product of said method, a method for the production of said intermediate, as well as use of said intermediate.

BACKGROUND OF THE INVENTION

Microfibrillated cellulose (MFC) is fibrous material comprised of cellulosic fibres, which are very thin, of a diameter of about 5 to 100 nm, in average about 20 nm, and have a fibre length of about 100 nm to 10 μm. Nanofibrillated cellulose (NFC) is a specific class of MFC with fibre dimensions at the low end of said fibre size range. MFC has a very large open active surface area, generally in the range of about 1 to 100 $m^2/g$, and is useful for a wide range of end used, notably in the field of papermaking.

Various known methods of microfibrillation of cellulosic fibres are summarized in U.S. Pat. No. 6,602,994 B1 as including e.g. homogenization, steam explosion, pressurization-depressurization, impact, grinding, ultrasound, microwave explosion, milling and combinations of these. Passing non-microfibrillar polysaccharide through a homogenizer at least three times is the preferred method according to this reference.

WO 2007/001229 adds to the above list enzyme treatment and, as a method of choice, oxidation in the presence of a transition metal for turning cellulosic fibres to MFC. After the oxidation step the material is taught to be disintegrated by mechanical means.

In most cases MFC is produced in an aqueous phase, and high quality MFC is produced typically as a slurry having a solid content of 1.5 to 2.5%. Due to the high open surface area and the high water bonding ability of MFC the viscosity of slurries of such low solid contents is already very high.

The low solids content makes delivery of MFC to customers uneconomical due to the large volumes being transported. This is one of the limiting factors in industrial MFC usage in large quantities. Furthermore, there are several applications where a high water content as such is a problem, for example manufacture of composites with plastics, asphalt, tires etc., as well as pillerizing.

An approach to solving the transport and high water content problems is drying the MFC product for the transport and rewetting or redispersing it at the end user. A problem of this procedure is a tendency for irreversible agglomeration (hornification) of the fibres in connection with drying, which would hamper subsequent redispersion of the same. Hornification can occur during drying of aqueous NFC suspensions or during compounding of NFC with hydrophobic polymers and it can be explained with the formation of a large number of hydrogen bonds between the hydroxyl groups of adjacent fibrils. This process is accompanied by a considerable decrease of the NFC aspect ratio and consequently results in the complete loss of its beneficial properties.

U.S. Pat. No. 4,481,076 teaches preparation of redispersible MFC by addition of substances capable of inhibiting hydrogen bonding between cellulose fibrils and then drying the product. In this way hornification would be avoided and regaining a high surface area would be secured, but the additives increase the cost of the product, and their presence may be harmful for various end uses of the product.

With an aim to reduce the amount of additives U.S. Pat. No. 6,231,657 B1 teaches preparation of NFC predominantly from primary walls of cellulosic fibres. Such NFC would be easily dispersible to an aqueous medium.

Water-redispersible NFC may be prepared in powder form e.g. by carboxymethylation and mechanical disintegration of refined, bleached chemical pulp. The powders will form stable gels when dispersed in water. Thus by carboxymethylation hornification of NFC can be successfully prevented during drying. The chemical modification of cellulose as required is expensive, however, and in some applications such modification is not accepted.

It is also known to dry MFC via solvent exchange and thus partially prevent hornification and fiber-to-fiber bonds. This way it is possible to regain high open surface area and bonding ability of the MFC when rewetted.

As MFC is comprised of very fine material there is also a considerable risk of dusting and the ensuing safety of handling problem. Drying of MFC due to its high open surface is also much more difficult than drying of ordinary cellulose fibres and required specialized equipment differing from that used for ordinary pulp drying. Dusting then is a handicap not only in drying but as well in rewetting at the end user's facilities.

An alternative approach of avoiding the transport problem would be to remove the entire MFC preparation process to be carried out by the end user. This would be highly costly and impractical, however, losing the benefits of large-scale production at a specialized factory. The pulp milling or disintegration steps are relatively simple and conceivably could be carried out at pulp mills, but the more demanding preparatory steps would destroy the overall economy of this approach.

There is thus a need for new more energy and cost efficient solutions for delivering MFC to end users, avoiding chemical modification and additives and allowing deliveries in a more simple and safe way.

SUMMARY OF THE INVENTION

The present invention has the purpose of providing a solution to the above problem, which satisfies the requirements of reducing the bulk of material being transported to the end user of MFC or NFC, maintaining the cost benefits of mass production, and providing a product, which is manageable for the end user without need of specialized equipment and procedures to obtain wetted or dispersed fibres. The solution according to the present invention is a process for the production of highly refined or microfibrillated cellulose, which comprises the steps of: (a) treating cellulosic fibres to remove at least a major part of the primary wall of the fibres, (b) drying the treated fibres, (c) rewetting the treated fibres, and (d) disintegrating the wetted fibres by mechanical means to obtain the final product.

The concept of the present invention bringing its benefits is to have the more demanding preparatory steps (a) and (b)

of the above process carried out at a specialized plant, then transport the dry intermediate product of step (b) to the end user, and finally having the end used to turn the intermediate product to the final MFC or NFC according to less demanding steps (c) and (d).

In certain aspects, the fibres are dried to a water content of less than 20 wt-% at step (b).

In certain aspects, at step (a) primary wall material is removed by mechanical refining, oxidation, preferably by use of peroxide or ozone, and/or enzymatically, preferably by use of cellulase enzyme. In certain aspects, at step (a) primary wall material is removed by mechanical defibrillation combined with oxidation and/or enzymatic treatment.

In certain aspects, MFC is produced at step (d) by use of a homogenizer and a fluidizer in succession.

In certain aspects of the present invention, dried cellulosic pulp is obtainable as an intermediate product of the foregoing process, wherein the dried cellulosic pulp has an average fibre length of at least 0.4 mm, while less than 50% of the primary wall material of natural untreated fibres is left in the intermediate product.

In certain aspects, the average fibre length of the dried cellulosic pulp is more than 70%, preferably more than 80%, more preferably more than 90% of the average fibre length of the untreated fibres the pulp has been made from.

In certain aspects, at most 5 wt-% of the dried cellulosic pulp has a content of fines with a fibre length less than 10 µm.

In certain aspects, the dried cellulosic pulp has a water content of less than 20 wt-%.

In certain aspects, the dried cellulosic pulp has a Shoppler-Riegler (SR) drainage resistance in the range of 20SR-50SR, preferably 20SR-40SR, more preferably 20SR-35SR.

In certain aspects, the dried cellulosic pulp has a wet zero-span tensile strength that is less than 60 Nm/g, preferably less than 50 Nm/g, more preferably less than 40 Nm/g. In certain aspects, the dried cellulosic pulp has a BET surface of more than 40 m$^2$/g, preferably more than 60 m$^2$/g.

In certain aspects, the dried cellulosic pulp is in the form of stacked sheets, ready for transport to a different location In certain aspects of the present invention, a method for the production of the dried cellulosic pulp comprises the steps of: (a) treating cellulosic fibres to remove at least a major part of the primary wall of the fibres, to obtain fibres with an average fibre length of at least 0.4 mm, and (b) drying the fibres obtained at step (a).

In certain aspects, the fibres are dried in step (b) to a water content of less than 20 wt-%.

In certain aspects, at step (a) primary wall material is removed by mechanical refining, oxidation, preferably by use of peroxide or ozone, and/or enzymatically, preferably by use of cellulase enzyme.

In certain aspects, at step (a) primary wall material is removed by mechanical defibrillation combined with oxidation and/or enzymatic treatment.

In certain aspects of the present invention, the dried cellulosic pulp according to certain aspects of the present invention is used for the production of highly refined or microfibrillated cellulose.

DESCRIPTION OF THE INVENTION

The present invention is a process for the production of highly refined or microfibrillated cellulose, which comprises: (a) treating cellulosic fibres to remove at least a major part of the primary wall of the fibres, (b) drying the treated fibres, (c) rewetting the treated fibres, and (d) disintegrating the wetted fibres by mechanical means to obtain the final product.

According to the finding of the present inventors by removing primary wall of the pulp fibres it is possible to produce material that can be turned to MFC or NFC without difficulty. Surprisingly this property, that is, suitability to MFC or NFC production, is preserved as the fibres are dried, as opposed to the prior art teachings, which warn of heavy hornification of the dried fibers, thus making the fibers unsuitable for MFC production.

Thereby there is provided an economical route for the end user to acquire and utilize MFC or NFC without the need of investing in expensive fibre pretreatment equipment. Only an apparatus for mechanical disintegration of the dry intermediate product is needed.

Thus the preferred way of practicing the present invention is that the fibres dried at step (b) are transported to be rewetted and disintegrated according to steps (c) and (d) at a different location. The fibres may be dried at step (b) to a water content of about 20 wt-% or less, suitably to about 15 wt-% or less.

There are different ways for the removal of the primary wall material at step (a). Such techniques include e.g. mechanical refining, oxidation, preferably by use of peroxide or ozone, enzymatic treatment, preferably by use of a cellulase enzyme, and mechanical defibrillation combined with oxidation and/or enzymatic treatment.

More specifically, the primary wall of the fibres can be removed by increasing the pre-treatment of the fibres. Thus, increased refining, preferable high consistency refining has been shown to be very effective. Also, oxidizing chemicals (Tempo ext.) or enzymes affecting celluloses and/or hemicellulose can be used, either alone or in combination with refining, preferable high consistency refining. It has been shown that the combination of enzymatic pre-treatment or oxidizing chemicals, mechanical pre-treatment, enzymatic treatment and a mechanical treatment is very effective when it comes to removing the primary walls of cellulosic fibres.

The cellulosic fibres used in the process according to the present invention are preferable fibres of kraft pulp, i.e. they have been treated according to the kraft process. It has been shown that the primary wall of the fibres in kraft pulp often prevents the fibres from forming fibrils. However, removal of the primary wall according to the teachings of the present invention turns kraft pulp very useful for making MFC or NFC.

Also other pulps can also be used, for example sulphite pulp or agro based fibres. Typically fibres with thin fibre walls are preferably used.

Due to increased initial wet strength it is possible to run the stock obtained at step (a) of the present invention in a pulp drying machine even when the solids content after wire section and press section is relatively low. It is also possible to reduce grammage of the web without problems. The pulp is also suitable for utilization in drying machines, where high shrinkage and high tension stretch is needed.

The preferred way of producing the microfibrillated cellulose (MFC or NFC) at step (d) is by use of a homogenizer and a fluidizer in succession.

As the general concept and teaching of the invention is to refine cellulose at two consecutive disintegration steps (a) and (d), with drying (b) and then rewetting (c) the fibres between said steps, the present invention is not strictly limited to the production of MFC and NFC but also includes production of highly refined cellulose of slightly larger particle size, the fibers having a diameter up to 500 nm or more and a length of 500 μm or more.

The intermediate product obtained at step (b) of the above-described process, which forms a part of the present invention, is a dried cellulosic pulp having an average fibre length of at least 0.4 mm, while less than 50% of the primary wall material of natural untreated fibres remains present in said product.

In the intermediate product the average fibre length may be more than 70%, preferably more than 80%, more preferably more than 90% of the average fibre length of the untreated fibres the product has been made from.

Preferably the intermediate product has a content of at most 5 wt-% of fines with a fibre length less than 10 μm and a water content of less than 20 wt-%.

Preferably the intermediate product has a Shoppler-Riegler (SR) drainage resistance, which is in the range of 20SR-50SR, preferably 20SR-40SR, and more preferably 20SR-35SR.

Preferably the intermediate product has a wet zero-span tensile strength, which is less than 60 Nm/g, preferably less than 50 Nm/g, and more preferably less than 40 Nm/g.

Preferably the intermediate product has a BET surface, which is more than 40 m$^2$/g, preferably more than 60 m$^2$/g.

The aim in the present invention is to avoid additives that could harm the final uses of the MFC product. Preferably the content of any substances added to the intermediate product for improving redispersability of the same is less than 1 wt-%.

The dried intermediate product can be in the form of stacked sheets, suitable for the transport to a different location.

The method of producing the dried cellulosic pulp described as an intermediate in the above comprises (a) treating cellulosic fibres to remove at least a major part of the primary wall of the fibres, to obtain fibres with an average fibre length of at least 0.4 mm, and (b) drying the fibres obtained at step (a). The various embodiments of this method correspond to the embodiments involving steps (a) and (b) of the method of producing the highly refined or microfibrillated cellulose as described above.

Use of the dried cellulosic pulp described as an intermediate in the above comprises use for the production of highly refined or microfibrillated cellulose, through the steps of rewetting and disintegration by mechanical means. Preferably these final steps are carried out at a location different from the location where the intermediate is produced.

The present invention is illustrated by means of the following examples, which are not to be construed as limiting the present invention, however.

EXAMPLES

Generally, as the starting material fibres of any kind of wood fibres, such as hardwood fibres or softwood fibres, and/or agricultural fibres may be used. The pretreatment can be mechanical treatment, such as disintegration, enzymatic treatment, carboxy methylation, TEMPO oxidation, CMC grafting, chemical swelling, acid hydrolysis or other methods which will facilitate the formation of microfibrillated cellulose. The pretreatment can be done in one or more steps.

For the tests bleached, pine kraft pulp was chosen as the starting material. The pretreatment was enzymatic, and the intermediate product was dried with air or in oven at 105° C. The intermediate product was turned to final MFC dispersion product by disintegration and fluidization.

As comparative examples, the same pine kraft pulp was used as wet (sample 1), dry (sample 2), and as pretreated but without being dried (sample 3). The examples according to the present invention are the kraft pulp pretreated and air dried (sample 4) and the kraft pulp pretreated and oven dried (sample 5).

For the pretreatment, the wet bleached kraft pine pulp was mixed in a 5 m$^3$ pulper in a consistency of 3.5-4.5%. The temperature of the pulp was adjusted to 50° C., and the pH was adjusted to 5.

A 250 ECU dosage of Endogluganace (EG) enzyme was added. Mixing was continued for 2.5 hours. After this the temperature was increased to 85° C. and pH adjusted to 10 in order to inactivate the enzyme. The enzymatically treated pulp was run though a pilot paper machine and dried as sheets with air to a moisture content of 37.2%. Part of the sheets were torn into pieces and dried in an oven at 105° C. for 19 h.

The results of measurements carried out for the dried intermediate product according to the present invention (samples 4 and 5) and the comparative materials (samples 1-3) are shown in Table 1.

The results show that the fibers have preserved over 85% of their original fiber length in the pretreatment. Such pretreated and dried intermediate product is free of a dusting problem. At the same time especially the drastically reduced zero-span tensile strength show a major change having taken place in the fibres. The low values mean that the fibres will disintegrate easily as the material is turned to MFC at the final steps. The SR drainage resistance values have grown, but not too much to prevent effective drying of the fibres on a moving web. Standard evaporation drying methods and devices used for normal pulps may be used for the drying.

The procedure was then continued by storing the dried pulp sample (5) in a plastic bag for one month. After this the dried pulp was dispersed in water to form a dispersion of 3% solids content and immediately disintegrated with 30000 revolutions in a standard laboratory disintegrator. The mass of each batch of pulp was 1488 g during the disintegration.

Immediately after disintegration, the pulp was fluidized in a microfluidizer, with an interaction chamber with a dimension of 400 μm and an auxiliary processing module with a hole dimension of 200 μm.

The runnability of this pulp in a paper machine was only slightly worse than the never-dried pretreated pulp (sample 3) of the same type. No plugging problems, however, appeared.

An inspection of photos of MFC made from never-dried pretreated pulp and MFC made from dried pretreated pulp as described (samples 3 and 5, respectively) here showed very little visual difference, but the measured viscosity of an aqueous dispersion of the latter appeared to be smaller than that of the former.

A comparative test was performed with the non-pretreated dried pulp (sample 2). The original fibre length of 2.2 mm was first reduced to about half by use of a Whiley mill. An attempt to turn wetted fibres into a fibrous dispersion in the laboratory disintegrator failed. At low solids contents the fibres were not gelled, and at higher solid contents the material did not pass the device. In a 78/22 wt-% mixture with standard MFC the comparative milled pulp was runnable, but was then left unaffected by the fluidizer. The pretreatment required in the present invention appears to be necessary for turning the starting material into MFC.

TABLE 1

| Pulp properties | Sample | | | | |
|---|---|---|---|---|---|
| | 1 | 2 | 3 | 4 | 5 |
| | never dried pine (ref) wet ref | dried pine (ref) dry reference | never dried pre-treated | dried pre-treated air drying | dried pre-treated oven dried (105° C.) |
| SR****) | 14.0 | 13.5 | 23.5 | 22.5 | 20.5 |
| Canadian Freenes | 645 | 655 | 430 | 430 | 465 |
| WRV 100 mesh**) | 170 | 116 | 162 | 148 | 140 |
| FiberLab***) | | | | | |
| Length length weighted | 2.1 mm | 2.2 mm | 1.96 mm | 1.92 mm | 1.95 mm |
| Fines length weighted | 3.2% | 2.9% | 4.3% | 4.6% | 4.0% |
| Zero span wet Nm/g*) | 112 | 114 | 31 | 30 | 30 |

*)ISO 15361:2000 (E) Pulps - Determination of zero-span tensile strength, wet or dry
**)SCAN-C 62:00 WRV
***)Fiberlab fiber analyzator - according to suppliers manual W4230467 V3.5 FI
****)ISO 5267/1 Pulps - Determination of drainability - Part 1: Shopper-Riegler method

The invention claimed is:

1. A method for the production of a highly refined cellulose product or a microfibrillated cellulose product, the method comprising the steps of:
   (a) treating cellulosic fibres having a primary wall material at a first location by mechanical refining, oxidation using peroxide or ozone and/or enzymatically to provide treated fibres having at least 50% of the primary wall material removed;
   (b) evaporation drying the treated fibres by use of an evaporation drying machine for pulp to obtain a dried cellulosic pulp intermediate product having a water content of less than 20 wt-%, a Shoppler-Riegler (SR) drainage resistance in the range of 20SR to 35SR, and a wet zero-span tensile strength less than 60 Nm/g;
   (c) transporting the dried cellulosic pulp intermediate product at step (b) in the form of two or more stacked sheets to a different second location;
   (d) rewetting at least one sheet of the dried cellulosic pulp intermediate product at the different second location to provide wetted fibres; and
   (e) disintegrating the wetted fibres by mechanical means to obtain the highly refined cellulose product or the microfibrillatd cellulose product, the highly refined cellulose product having a diameter up to 500 nm and a fibre length of at least 500 µm, and the microfibrillated cellulose product having a diameter of about 5 to 100 nm and a fibre length of about 100 nm to 10 µm.

2. The method of claim 1, wherein at step (a) the primary wall material of the cellulosic fibres is removed by mechanical refining.

3. The method of claim 1, wherein at step (a) the primary wall material of the cellulosic fibres is removed by oxidation using peroxide or ozone.

4. The method of claim 1, wherein at step (a) the primary wall material of cellulosic fibres is removed enzymatically by the use of a cellulase enzyme.

5. The method of claim 1, wherein the primary wall material of cellulosic fibres is removed by mechanical defibrillation combined with oxidation using peroxide or ozone and/or enzymatic treatment.

6. The method of claim 1, wherein at step (a) cellulosic fibres are treated enzymatically or by oxidation to remove at least 50% of the primary wall material to provide the treated fibres having an average fibre length of at least 0.4 mm.

7. The method of claim 6 wherein at step (a) the primary wall material is removed by mechanical refining.

8. The method of claim 6, wherein the primary wall material is removed by mechanical defibrillation combined with oxidation using peroxide or ozone and/or enzymatic treatment.

9. The method of claim 1, wherein the dried cellulosic pulp intermediate product has a BET surface of more than 40 m²/g.

10. The method of claim 1, wherein the cellulosic fibres are selected from the group consisting of hardwood fibres, softwood fibres, and agricultural fibres.

11. The method of claim 1, wherein the mechanical means of disintegrating the wetted fibres of step (e) comprises a homogenizer.

12. A method for the production of a highly refined cellulose product or a microfibrillated cellulose product, the method comprising the steps of:
   (a) treating cellulosic fibres having a primary wall material at a first location by mechanical refining, oxidation using peroxide or ozone and/or enzymatically to provide treated fibres having at least 50% of the primary wall material removed;
   (b) evaporation drying the treated fibres by use of an evaporation drying machine for pulp to obtain a dried cellulosic pulp intermediate product having a water content of less than 20 wt-% a Shoppler-Riegler (SR) drainage resistance in the range of 20SR to 35SR, an average fibre length of at least 0.4 mm, and a wet zero-span tensile strength less than 60 Nm/g;
   (c) transporting the dried cellulosic pulp intermediate product at step (b) in the form of two or more stacked sheets to a different second location;
   (d) rewetting at least one sheet of the dried cellulosic pulp intermediate product at the different second location to provide wetted fibres; and
   (e) disintegrating the wetted fibres by mechanical means to obtain the highly refined cellulose product or the microfibrillatd cellulose product, the highly refined cellulose product having a diameter up to 500 nm and a fibre length of at least 500 µm, and the microfibrillated cellulose product having a diameter of about 5 to 100 nm and a fibre length of about 100 nm to 10 μm.

13. The method of claim 12, wherein the wet zero-span tensile strength of the dried cellulosic pulp intermediate product of step (b) is less than 40 Nm/g.

14. The method of claim 12, wherein the dried cellulosic pulp intermediate product of step (b) has a BET surface of more than 40 m$^2$/g.

15. The method of claim 12, wherein the dried cellulosic pulp intermediate product of step (b) is in the form of stacked sheets, ready for transport to a different location.

16. The method of claim 12, wherein the average fibre length of the dried cellulosic pulp intermediate product of step (b) is more than 70% of the average fibre length of the untreated cellulosic fibres.

17. The method of claim 12, wherein a content of fines with a fibre length less than 10 μm of the dried cellulosic pulp intermediate product of step (b) is at most 5 wt-%.

18. The method of claim 12, wherein the dried cellulosic pulp intermediate product of step (b) has a water content of less than 15 wt-%.

\* \* \* \* \*